(12) United States Patent
Triplett, II et al.

(10) Patent No.: US 6,395,933 B1
(45) Date of Patent: May 28, 2002

(54) PROCESS FOR PREPARING 4-AMINODIPHENYLAMINE INTERMEDIATES

(75) Inventors: Ralph Dale Triplett, II, Wadsworth; Roger Keranen Rains, Richfield, both of OH (US)

(73) Assignee: Flexsys America, L.P., Akron, OH (US)

( * ) Notice: Subject to any disclaimer, the term of this patent is extended or adjusted under 35 U.S.C. 154(b) by 0 days.

(21) Appl. No.: 09/911,058

(22) Filed: Jul. 23, 2001

(51) Int. Cl.$^7$ .............................................. C07C 209/36
(52) U.S. Cl. ................. 564/420; 564/421; 564/422; 564/423; 564/398; 564/397; 564/408; 564/433; 564/434
(58) Field of Search ................ 564/420, 421, 564/422, 423, 398, 397, 408, 433, 434

(56) References Cited

U.S. PATENT DOCUMENTS

| | | | |
|---|---|---|---|
| 5,117,063 A | | 5/1992 | Stern et al. ................. 564/398 |
| 5,453,541 A | | 9/1995 | Stern et al. ................. 564/398 |
| 5,608,111 A | * | 3/1997 | Stern et al. |
| 5,623,088 A | | 4/1997 | Stern et al. ................. 546/112 |
| 5,739,403 A | * | 4/1998 | Reinartz et al. |
| 5,932,768 A | | 8/1999 | Ooms et al. ................. 564/416 |
| 5,994,584 A | | 11/1999 | Ooms et al. ................. 564/416 |

FOREIGN PATENT DOCUMENTS

| | | | |
|---|---|---|---|
| EP | 566 783 | 10/1993 | ......... C07C/209/02 |
| EP | 895 983 | 2/1999 | ......... C07C/209/36 |
| EP | 941 985 | 9/1999 | ......... C07C/209/36 |
| WO | WO 98/56751 | 12/1998 | ......... C07C/209/36 |
| WO | WO 99/59956 | 11/1999 | ......... C07C/209/36 |
| WO | WO 00/35853 | 6/2000 | ......... C07C/209/36 |
| WO | WO 01/14312 | 3/2001 | ......... C07C/211/56 |

OTHER PUBLICATIONS

Derwent Abstract No. 755723 abstracting New method for preparing p–nitrodiphenylamine, Huaxue Tongbao, 1996, (vol. 10), pp. 42–43, Wei C. et al.
Derwent Abstract 98–205223/18 abstracting RD 407033.
Abstract No. 1986:224682 abstracting CZ 218720B.

* cited by examiner

*Primary Examiner*—Samuel Barts
(74) *Attorney, Agent, or Firm*—Louis A. Morris

(57) ABSTRACT

The invention is directed to a method of producing one or more 4-aminodiphenylamine intermediates comprising the steps of bringing an aniline or aniline derivative and nitrobenzene into reactive contact; and reacting the aniline and nitrobenzene in a confined zone at a suitable time and temperature, in the presence of a mixture comprising a strong base and a suitable phase transfer catalyst. Certain phase transfer catalysts may also function as the strong base.

26 Claims, No Drawings

PROCESS FOR PREPARING 4-AMINODIPHENYLAMINE INTERMEDIATES

BACKGROUND OF THE INVENTION

1. Field of the Invention

The present invention relates to a process for preparing 4-aminodiphenyl-amines intermediates.

2. Related Art

4-Aminodiphenylamines are widely used as intermediates in the manufacture of alkylated derivatives having utility as antiozonants and antioxidants, as stabilizers for monomers and polymers, and in various specialty applications. For example, reductive alkylation of 4-aminodiphenylamine (4-ADPA) with methylisobutyl ketone provides N-(1,3-dimethylbutyl)-N'-phenyl-p-phenylene-diamine, which is a useful antiozonant for the protection of various rubber products.

4-Aminodiphenylamine derivatives can be prepared in various ways. An attractive synthesis is the reaction of an optionally substituted aniline with an optionally substituted nitrobenzene in the presence of a base, as disclosed, for example, in U.S. Pat. No. 5,608,111 (to Stern et al.) and U.S. Pat. No. 5,739,403 (to Reinartz et al.).

U.S. Pat. No. 5,608,111 describes a process for the preparation of an optionally substituted 4-ADPA wherein in a first step optionally substituted aniline and optionally substituted nitrobenzene are reacted (coupled) in the presence of a base. In working examples, aniline and nitrobenzene are reacted in the presence of tetramethylammonium hydroxide as the base, and water and aniline are azeotropically removed during the coupling reaction.

International publication WO 00/35853 discloses a method of preparation of intermediates of 4-aminodiphenylamine by the reaction of aniline with nitrobenzene in a liquid medium where the reaction system consists of a solution of salts of true zwitterions with hydroxides. A combination of potassium hydroxide and betaine hydrate is exemplified. The reaction may take place in the presence of free oxygen.

EP publication 566 783 describes a method of manufacture of 4-nitrodiphenylamine by the reaction of nitrobenzene with aniline in the medium of a polar aprotic solvent in a strongly alkaline reaction system. A phase transfer catalyst such as tetrabutylammonium hydrogen sulfate is employed. This reference requires that the reaction be carried out in an oxygen-free atmosphere in order to prevent undesirable side reactions caused by oxidation.

U.S. Pat. No. 5,117,063 and International publication WO 01/14312 disclose processes processes for preparing 4-nitrodiphenylamine and 4-nitrosodiphenhlamine, using an inorganic base with crown ether, a phase transfer catalyst.

The objective of the present invention is to provide a superior method for producing one or more 4-ADPA intermediates by reacting aniline and nitrobenzene in the presence of a strong base and a phase transfer catalyst.

SUMMARY OF THE INVENTION

In brief summary, the primary embodiment of the present invention is for a method of producing one or more 4-aminodiphenylamine intermediates comprising the steps of:

(a) bringing an aniline or aniline derivative and nitrobenzene into reactive contact; and (b) reacting the aniline and nitrobenzene in a confined zone at a suitable time and temperature, in the presence of a mixture comprising a strong base, an oxidant and a phase transfer catalyst selected from the group of compounds defined by (b) reacting the aniline and nitrobenzene in a confined zone at a suitable time and temperature, in the presence of a mixture comprising a strong base, an oxidant, and a phase transfer catalyst selected from the group of compounds defined by:

I

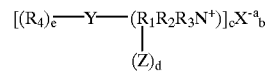

where $R_1$, $R_2$, $R_3$ are the same or different and selected from any straight chain or branched alkyl group containing from $C_1$ to $C_{20}$, $(R_4)_e$ is hydrogen for e=0, $R_4$ is $R_1R_2R_3N^+$ for e=1 or 2, Y is alkyl, aryl, alkyl aryl or benzyl and substituted derivatives thereof, Z is a substituent selected from the group consisting of hydroxyl, halo, and other hetero atoms, X is an anionic moiety of the form fluoride, chloride, hydroxide, sulfate, hydrogensulfate, acetate, formate, nitrate, phosphate, hydrogen phosphate, dihydrogenphosphate, oxalate, carbonate, borate, tartrate, citrate, malonate and mixtures of said compounds, where a=the valence of the anionic moiety (1, 2 or 3), b and c are whole number integers of value 1, 2 or 3 and d is a whole number integer of value 0 to 4.

Other embodiments of the present invention encompass details about reaction mixtures and ratios of ingredients, particular phase transfer catalysts and particular strong bases, all of which are hereinafter disclosed in the following discussion of each of the facets of the present invention.

DETAILED DESCRIPTION OF THE INVENTION

The present invention is directed to a method, as described above, for making intermediates of 4-ADPA that has superior yield and selectivity for those intermediates. Such intermediates comprise 4-nitroso- and/or 4-nitrodiphenylamines (p-NDPA and 4-NDPA, respectively) and salts thereof. The intermediates may then be hydrogenated to produce 4-aminodiphenylamine.

An example of a substituted and multifunctional phase transfer catalyst that is consistent with the above formula I is (2S, 3S)-bis(trimethylammonio)-1,4-butanediol dichloride. Other effective phase transfer catalysts fitting formula 1, in addition to those shown in the following examples, can be derived from examples in the literature, such as C. M. Starks and C. Liotta, Phase Transfer Catalysis, Principles and Techniques, Academic Press, 1978 and W. E. Keller, Fluka-Compendium, Vol. 1,2,3, Georg Thieme Verlag, New York, 1986, 1987, 1992.

Phase transfer catalysts known or believed to be particularly effective in the method of the invention include tetramethylammonium chloride, tetramethylammonium fluoride, tetramethylammonium hydroxide, bis-tetramethylammonium carbonate, tetramethylammonium formate and tetramethylammonium acetate; tetrabutylammonium hydrogensulfate and tetrabutylammonium sulfate; methyltributylammonium chloride; and benzyltrimethylammonium hydroxide (Triton B), tricaprylylmethylammonium chloride (Aliquat 336), tetrabutylammonium chloride, tetramethylammonium nitrate, cetyltrimethylammonium chloride and choline hydroxide .

Phase transfer catalysts of the present invention have several advantages over crown ethers, such as 18-crown-6, which were described as effective with alkali metal hydroxides in references such as U.S. Pat. No. 5,117,063 and International publication WO 01/14312 discussed above. The most obvious disadvantages of crown ethers are very high initial cost and high toxicity. In addition, most crown ethers have poor solubility in water, so they cannot be recovered for recycle with an aqueous base stream. Furthermore, the boiling points of crown ethers are high enough that they cannot be recovered by distillation without an extra distillation step. Even for the class of crown ethers that have good solubility in water, solubility in organics is also good, so that there will be a high loss to the organic product stream. Finally, crown ethers are known chelating agents, so that there is a high probability of unacceptable loss of expensive hydrogenation catalyst metal, due to complexation with the crown ether.

In the method of the invention, the molar ratio of phase transfer catalyst to nitrobenzene reactant is preferably from about 0.05:1 to about 1.2:1.

While aniline most effectively couples with nitrobenzene, certain aniline derivatives comprising amides such as formanilide, phenylurea and carbanilide as well as the thiocarbanilide can be substituted to produce 4-ADPA intermediates.

Although the reactants of the method of the invention are referred to as "aniline" and "nitrobenzene", and when it is 4-ADPA that is being manufactured the reactants are in fact aniline and nitrobenzene, it is understood that the reactants may also comprise substituted aniline and substituted nitrobenzene. Typical examples of substituted anilines that may be used in accordance with the process of the present invention include but are not limited to 2-methoxyaniline, 4-methoxy-aniline, 4-chloroaniline, p-toluidine, 4-nitroaniline, 3-bromoaniline, 3-bromo-4-aminotoluene, p-aminobenzoic acid, 2,4-diaminotoluene, 2,5-dichloroaniline, 1,4-phenylene diamine, 4,4'-methylene dianiline, 1,3,5-triaminobenzene, and mixtures thereof. Typical examples of substituted nitrobenzenes that may be used in accordance with the process of the present invention include but are not limited to o- and m-methylnitrobenzene, o- and m-ethylnitrobenzene, o- and m-methoxynitrobenzene, and mixtures thereof.

The method of the invention will hereinafter be described with reference to the manufacture of 4-ADPA itself, starting from aniline and nitrobenzene.

The molar ratio of aniline to nitrobenzene in the process according to the present invention is not particularly important, the process will be effective with an excess of either.

Strong bases particularly effective in the process of the present invention include potassium hydroxide, sodium hydroxide, cesium hydroxide, rubidium hydroxide and potassium-t-butoxide. It is preferred that mole ratio of strong base to nitrobenzene is greater than about 1:1. A particularly preferred mole ratio of strong base to nitrobenzene is about 2:1 to about 6:1.

The reactive contact of the process of the invention is carried out in the presence of an oxidant. The oxidant may be free oxygen, or an oxidizing agent such as hydrogen peroxide. Nitrobenzene may also function as an oxidizing agent.

The reactive contact may be carried out at a temperature of from about 20° C. to about 125° C. Other conditions for the reactive contact include pressures in the range of from about 20 mbar to about atmospheric. Reaction time is typically less than about 3.5 hours. It is advantageous to agitate the reaction mixture during the entire reaction.

The reaction of step (b) of the present method may be carried out in the presence of not greater than about 10:1 moles water to moles nitrobenzene. The amount of water does not include the water that hydrates with the reactants and/or with compounds formed in the process. When the reaction mixture comprising a strong base and a phase transfer catalyst is in aqueous solution, the reaction may be carried out with a continuous distillation of aniline-water azeotrope.

The aqueous phase may be reused to form a new reaction mixture. Fresh base is added to replace base lost by decomposition, by-product formation and solubility in the separated organic phase. Excess Aniline recovered by distillation from the reaction product mixture may be combined with make-up fresh aniline for recycle to form a new reaction mixture. Recovery of excess nitrobenzene is preferably carried out prior to hydrogenation of the 4-ADPA intermediate by a separation step and the recovered nitrobenzene may be hydrogenated to aniline for use in the process.

The method of the present invention for the preparation of 4-aminodiphenylamines intermediates may be conducted as a batch process or may be performed continuously using means and equipment well known to the skilled person.

The reactive contact in step (a) of the method of the invention may occur in a suitable solvent system. A suitable solvent system comprises a polar aprotic solvent. The polar aprotic solvent may be selected form the group consisting of dimethyl sulfoxide, benzyl ether, 1-Methyl-2-pyrrolidinone and N, N-dimethylformamide.

The invention includes a method where the strong base also functions as a phase transfer catalyst and the reaction may be in the absence of an alkali metal hydroxide. In that case the phase transfer catalyst may be selected from the group of compounds defined by:

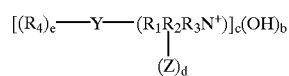

I where $R_1$, $R_2$, $R_3$ are the same or different and selected from any straight chain or branched alkyl group containing from $C_1$ to $C_{20}$, $(R_4)[<i]nfe$ is hydrogen for e=0, $R_4$ is $R_1R_2R_3N^+$ for e=1 or 2, Y is alkyl, aryl, alkyl aryl or benzyl and substituted derivatives thereof, Z is a substituent selected from the group consisting of hydroxyl, halo, and other hetero atoms, b and c are whole number integers of value 1, 2 or 3 and d is a whole number integer of value 0 to 4.

The invention is illustrated by the following examples.

Experimental conditions are detailed within individual examples. In all examples the charging of reactors was performed in open air resulting in some free oxygen being present during the reactions, except for experiments, where indicated, run for comparative purposes. No attempt was made to remove water from the reaction mixtures.

ANALYTICAL

Yields of individual components were determined by external standard HPLC. Approximately 0.6 grams of material to be analyzed is accurately weighed into a 50-mL volumetric flask and diluted with a buffer solution containing 39% v/v water, 36% v/v acetonitrile, 24% v/v methanol and 1% v/v pH 7 buffer. The solution is injected through a 10 μL loop onto a reversed phase Zorbax ODS HPLC column (250×4.6 mm) using a binary gradient pumping system and the following elution gradient at a constant flow rate of 1.5 mL/minute:

| Time, minutes | % A | % B |
|---|---|---|
| 0 | 100 | 0 |
| 25 | 25 | 75 |
| 35 | 0 | 100 |
| 37.5 | 0 | 100 |
| 38 | 100 | 0 |
| 40 | 100 | 0 |

Eluent A is 75% v/v water, 15% v/v acetonitrile and 10% v/v methanol. Eluent B is 60% v/v acetonitrile and 40% v/v methanol. Detection is UV at 254 nm.

Nitrobenzene conversion is calculated by sum addition of known components plus any unknown peaks (assigned an arbitrary mole weight value of 216, aniline+nitrobenzene) as analyzed. In some instances, sum conversion is greater than 100% due to the formation of derivatives from aniline only.

Selectivity is defined by the formula: (p-NDPA Yield+4-NDPA Yield)/Conversion where 4-NDPA is 4-nitrodiphenylamine and p-NDPA is 4-nitrosodiphenylamine.

In the tables: "An Recr" refers to compounds from which aniline may be easily recovered and is a sum total of trans-azobenzene and azoxybenzene; "Others" are aniline and nitrobenzene coupling by-products e.g. phenazine, N-oxy-phenazine, 2-NDPA, 4-phenazo-diphenylamine and any unknowns.

EXPERIMENTAL

Experimental conditions are detailed within individual examples.

EXAMPLE 1

Example 1 illustrates that 4-ADPA intermediates may be formed from aniline and nitrobenzene in the presence of an inorganic base (potassium hydroxide) and phase transfer catalyst (tetramethylammonium chloride, TMACl) in a solvent-free system under relatively mild conditions. Yield of desired products is dependent on the amount of phase transfer catalyst added.

Aniline (99%, 22.58 grams, 240 mmoles), nitrobenzene (99%, 4.97 grams, 40 mmoles), potassium hydroxide (86% ground powder, 7.83 grams, 120 mmoles) and tetramethylammonium chloride were charged to a 50-mL round bottomed flask equipped with magnetic stirrer in the amount indicated in Table 1 below. The reaction wasallowed to proceed for 1 hour at 60° C. in a stoppered flask. Contents were then sampled and analyzed by HPLC.

TABLE 1

| | Yield, % | | | | |
|---|---|---|---|---|---|
| | Conversion | p-NDPA | 4-NDPA | An Recr | Other |
| No TMACl added, KOH Only | 26.3% | 0.8 | 4.8 | 5.5 | 15.2 |
| 1.81 grams TMACl, 16 mmoles (0.4 vs NB) | 59.2% | 10.9 | 26.9 | 18.4 | 3.0 |
| 3.62 grams TMACl, 32 mmoles (0.8 vs NB) | 90.1% | 22.4 | 36.1 | 28.6 | 3.0 |
| 5.42 grams TMACl, 48 mmoles (1.2 vs NB) | 98.2% | 27.0 | 37.8 | 30.3 | 3.0 |
| 7.23 grams TMACl, 64 mmoles (1.6 vs NB) | 94.4% | 26.5 | 36.2 | 28.9 | 2.9 |
| 9.04 grams TMACl, 80 mmoles (2.0 vs NB) | 98.9% | 26.2 | 36.7 | 31.8 | 4.2 |

Similar results were obtained when running the reaction under slightly varying conditions (equimolar An/NB, higher reaction temperature, longer cycle time, water addition, etc.) as given below in Table 2.

Aniline (99%, 2.33 grams, 24.8 mmoles), nitrobenzene (99%, 3.08 grams, 24.8 mmoles), potassium hydroxide (86% ground powder, 9.77 grams, 150 mmoles), tetramethylammonium chloride (97%, see Table 2) and water (Table 2) were charged to a 50-mL round bottomed flask equipped with magnetic stirrer. The water amount was 20% by weight of total reactor charge assuming 14% w/w $H_2O$ from KOH. The reaction was allowed to proceed for 2 hours at 80° C. in an open flask. Contents were then sampled and analyzed by HPLC.

TABLE 2

| | Yield, % | | | | |
|---|---|---|---|---|---|
| | Conversion | p-NDPA | 4-NDPA | An Recr | Other |
| No TMACl, KOH Only & 2.15 g $H_2O$ | 2.3% | 0.0 | 0.4 | 0.4 | 1.5 |
| 0.17 g TMACl, 1.5 mmoles (.06 vs NB) & 2.19 g $H_2O$ | 8.1% | 0.3 | 5.9 | 0.7 | 1.2 |
| 0.34 g TMACl, 3.0 mmoles (.12 vs NB) & 2.23 g $H_2O$ | 14.7% | 0.7 | 12.7 | 0.3 | 1.0 |
| 0.69 g TMACl, 6.1 mmoles (.25 vs NB) & 2.32 g $H_2O$ | 34.4% | 1.7 | 27.7 | 2.9 | 2.1 |
| 1.03 g TMACl, 9.1 mmoles (.37 vs NB) & 2.41 g $H_2O$ | 47.5% | 1.6 | 39.5 | 4.2 | 2.2 |
| 1.37 g TMACl, 12.1 mmoles (.49 vs NV) & 2.49 g $H_2O$ | 57.8% | 2.6 | 46.7 | 5.2 | 3.3 |
| 2.06 g TMACl, 18.2 mmoles (.74 vs NB) & 2.67 g $H_2O$ | 89.6% | 7.6 | 61.3 | 17.7 | 3.0 |
| 2.75 g TMACl, 24.3 mmoles (.98 vs NB) & 2.84 g $H_2O$ | 92.2% | 11.9 | 64.9 | 13.4 | 2.0 |

The yield of 4-ADPA intermediates was increased from<1% when no tetramethylammonium chloride was used to almost 77% when a near equimolar amount of phase transfer catalyst vs. nitrobenzene was added.

In both instances, more p-NDPA relative to 4-NDPA was produced as the tetramethylammonium chloride charge was increased. Also, more p-NDPA was formed in the presence of excess aniline (see Example 7).

EXAMPLE 2

Example 2 demonstrates that any of several phase transfer catalysts may be used with KOH to produce p-NDPA and 4-NDPA from aniline and nitrobenzene. Results are arranged in order of descending yield.

Charge to 50-mL round bottomed flask equipped with magnetic stirrer: aniline (99%, 22.58 grams, 240 mmoles), nitrobenzene (99%, 4.97 grams, 40 mmoles), potassium hydroxide (86% ground powder, 7.83 grams, 120 mmoles) and the indicated phase transfer catalyst given in Table 3 below where the amount of phase transfer catalyst is equal to the limiting reagent charge. (NOTE: Some experiments run on 20 or 30 mmole scale as denoted.) Reaction allowed to proceed for 1 hour at 60° C. in a stoppered flask. Contents then sampled and analyzed by HPLC.

chloride; and benzyltrimethylammonium hydroxide (Triton B) are most effective as phase transfer catalysts in combination with an inorganic base. Others such as tricaprylylmethylammonium chloride (Aliquat 336), tetrabutylammonium chloride, tetramethylammonium nitrate, and choline hydroxide are moderately efficient. Bromide and iodide salts and the zwitterion betaine are not as suitable. Periodic trends are observed for the tetramethylammonium salts as yield, conversion and selectivity are all decreased when going down in the series from fluoride to iodide.

EXAMPLE 3

Example 3 shows that nitrobenzene may be coupled with a variety of aniline derivatives to produce 4-ADPA intermediates.

A stoichiometric amount of substrate as listed in Table 4 below, nitrobenzene (99%, 3.08 grams, 24.8 mmoles), potassium hydroxide (86% ground powder, 9.77 grams, 150 mmoles), tetramethylammonium chloride (97%, 2.74 grams,

TABLE 3

|  | Conversion | p-NDPA | 4-NDPA | An Recr | Other |
|---|---|---|---|---|---|
| Tetrabutylammonium sulfate, 75% aq., 15.39 gms^ | 99.2% | 56.1 | 21.2 | 20.1 | 1.8 |
| Tetrabutylammonium hydrogensulfate, 97%, 10.50 gms* | 96.6% | 47.9 | 25.0 | 21.2 | 2.4 |
| Tetramethylammonium carbonate, 60% aq., 6.94 gms^ | 97.6% | 46.6 | 24.6 | 23.7 | 2.8 |
| Tetramethylammonium fluoride.4H$_2$O, 98%, 6.74 gms | 103.6% | 42.4 | 27.2 | 27.4 | 6.6 |
| Tetramethylammonium acetate, 95%, 5.61 gms | 104.3% | 25.9 | 43.1 | 35.0 | 0.4 |
| Tetramethylammonium hydroxide.5H$_2$O, 97%, 7.47 gms | 105.0% | 38.4 | 29.6 | 30.4 | 6.5 |
| Tetramethylammonium chloride, 97% aq., 4.52 gms | 98.8% | 24.3 | 37.1 | 30.8 | 6.6 |
| Methyltributylammonium chloride, 75% aq., 12.58 gms | 81.7% | 23.5 | 30.6 | 22.2 | 5.4 |
| Tetramethylammonium formate, 50% aq., 9.53 gms | 74.9% | 29.0 | 23.8 | 21.0 | 1.1 |
| Benzyltrimethylammonium hydroxide, 40% aq., 16.73 gms | 52.5% | 39.6 | 6.2 | 5.5 | 1.2 |
| Tricaprylylmethylammonium chloride, 99+%, 16.17 gms | 67.0% | 19.1 | 21.3 | 19.6 | 7.0 |
| Tetramethylammonium nitrate, 96%, 5.67 gms | 61.3% | 12.0 | 27.4 | 19.6 | 2.4 |
| Choline hydroxide, 50% aq., 9.69 gms | 59.0% | 26.2 | 6.7 | 19.6 | 6.6 |
| Tetrabutylammonium chloride.H2O, 98%, 8.51 gms* | 42.6% | 8.2 | 23.8 | 9.3 | 1.2 |
| Betaine, 98%, 4.78 gms | 55.0% | 13.0 | 17.2 | 19.6 | 5.2 |
| Cetyltrimethylammonium bromide, 95%, 11.51 gms* | 36.2% | 7.0 | 19.3 | 8.7 | 1.1 |
| Tetramethylammonium bromide, 98%, 6.29 gms | 36.5% | 11.3 | 12.2 | 6.7 | 6.3 |
| Tetrabutylammonium bromide, 99%, 13.03 gms | 34.1% | 8.3 | 14.2 | 5.8 | 5.7 |
| Polyethylene glycol (MW ≈ 200), 8.00 gms | 33.4% | 11.9 | 0.6 | 17.2 | 3.7 |
| Tetramethylammonium iodide, 99%, 8.12 gms | 27.8% | 2.4 | 8.0 | 5.8 | 11.6 |
| Tetrabutylphosphonium bromide, 98%, 13.58 gms | 25.6% | 1.6 | 5.1 | 9.4 | 10.0 |
| KOH Only, No phase transfer catalyst added | 19.6% | 1.2 | 4.0 | 3.3 | 11.0 |

*30 mmole scale (16.93 gms aniline, 3.73 gms nitrobenzene, 5.87 gms KOH & PTC as listed)
^20 mmoles (TMA)$_2$CO$_3$ & (TBA)$_2$SO$_4$ (0.5 to 1 vs NB, same no. of equivalents)

Results in Table 3 above illustrate that the addition of a phase transfer catalyst improves the yield of desired products in all cases. Tetramethylammonium chloride, fluoride, hydroxide, carbonate, formate and acetate; tetrabutylammonium hydrogensulfate and sulfate; methyltributylammonium 24.3 mmoles), and water (2.84 grams) were charged to a 50-mL round bottomed flask equipped with a magnetic stirrer. The reaction was allowed to proceed for 2 hours at 80° C. in an open flask. Contents were then sampled and analyzed by HPLC.

TABLE 4

|  | | Yield, % | | | |
|---|---|---|---|---|---|
|  | Conversion | p-NDPA | 4-NDPA | An Recr | Other |
| Aniline, 99%, 2.33 grams, 24.8 mmoles | 95.4% | 6.0 | 68.3 | 19.9 | 1.2 |
| Formanilide, 99%, 3.03 grams, 24.8 mmoles | 84.5% | 19.3 | 47.3 | 16.3 | 1.5 |
| Phenylurea, 97%, 3.40 grams, 24.2 mmoles | 96.2% | 19.2 | 38.8 | 13.5 | 24.8 |

TABLE 4-continued

|  | Yield, % | | | | |
|---|---|---|---|---|---|
|  | Conversion | p-NDPA | 4-NDPA | An Recr | Other |
| Carbanilide, 98%, 2.65 grams, 12.2 mmoles | 48.1% | 1.3 | 37.1 | 9.3 | 0.4 |
| Thiocarbanilide, 98%, 2.85 grams, 12.2 mmoles | 58.6% | 5.4 | 31.6 | 18.6 | 3.0 |
| Acetanilide, 97%, 3.38 grams, 24.3 mmoles | 8.5% | 0.3 | 2.7 | 3.6 | 1.9 |
| Benzamide, 99%, 3.03 grams, 24.8 mmoles | 49.4% | 0.0 | 1.0 | 15.1 | 33.3 |
| N-Methyl-Benzamide, 99+%, 3.38 grams, 25.0 mmoles | 8.2% | 0.0 | 0.0 | 0.0 | 8.2 |
| Benzanilide, 98%, 2.47 grams, 12.3 mmoles | 0.1% | 0.0 | 0.1 | 0.0 | 0.0 |

While aniline most effectively couples with nitrobenzene in a KOH-TMACl system, amides such as formanilide, phenylurea and carbanilide as well as the thiocarbanilide can be substituted to produce 4-ADPA intermediates.

EXAMPLE 4

Example 4 illustrates the reaction of aniline and nitrobenzene using various bases in combination with tetramethylammonium chloride to produce 4-ADPA intermediates.

Aniline (99%, 22.58 grams, 240 mmoles), nitrobenzene (99%, 4.97 grams, 40 mmoles), an appropriate amount of base as given in Table 5 below and tetramethylammonium chloride (97%, 4.52 grams, 40 mmoles) was charged to a 50-mL round bottomed flask equipped with a magnetic stirrer. The reaction was allowed to proceed for 1 hour at 60° C. in a stoppered flask. Contents were then sampled and analyzed by HPLC.

TABLE 5

|  | Yield, % | | | | |
|---|---|---|---|---|---|
|  | Conversion | p-NDPA | 4-NDPA | An Recr | Other |
| KOH, 86%, 7.83 grams, 120 mmoles (3:1 vs NB) | 97.1% | 25.2 | 35.5 | 30.6 | 5.8 |
| KOH, 86%, 13.05 grams, 200 mmoles (5:1 vs NB) | 100.5% | 21.5 | 36.0 | 32.0 | 11.0 |
| NaOH, 98%, 4.90 grams, 120 mmoles (3:1 vs NB) | 21.3% | 4.7 | 12.6 | 3.4 | 0.6 |
| NaOH, 98%, 8.16 grams, 200 mmoles (5:1 vs NB) | 50.4% | 11.5 | 24.5 | 14.2 | 0.2 |
| CsOH.H$_2$O, 95%, 15.91 grams, 90 mmoles (3:1 vs NB)* | 98.8% | 20.5 | 43.2 | 34.5 | 0.6 |
| t-BuOK, 95%, 11.84 grams, 100 mmoles (2½:1 vs NB) | 107.1% | 15.2 | 33.4 | 25.0 | 33.5 |
| TMAH.5H$_2$O, 22.42 grams, 120 mmoles (3:1 vs NB)^ | 51.5% | 38.2 | 7.0 | 5.9 | 0.4 |

*30 mmole scale (16.93 gms aniline, 3.73 gms nitrobenzene, 3.39 gms TMACl & base as indicated)
^Tetramethylammonium hydroxide only. No TMACl added.

Both lithium and calcium hydroxide were screened with no reaction observed for either of these two bases.

Potassium hydroxide is the preferred base but sodium hydroxide, cesium hydroxide, potassium t-butoxide and tetramethylammonium hydroxide are also suitable bases any of which may used in combination with tetramethylammonium chloride to obtain acceptable rates of conversion.

EXAMPLE 5

Example 5 demonstrates the effect of increasing potassium hydroxide charge on aniline-nitrobenzene coupling products under otherwise constant reaction conditions with tetramethylammonium chloride as a phase transfer catalyst.

Aniline (99%, 22.58 grams, 240 mmoles), nitrobenzene (99%, 4.97 grams, 40 mmoles), potassium hydroxide in the amount given in Table 6 below and tetramethylammonium chloride (97%, 4.52 grams, 40 mmoles) was charged to a 50-mL round bottomed flask equipped with magnetic stirrer. The reaction was allowed to proceed for 1 hour at 60°C. in a stoppered flask. Contents were then sampled and analyzed by HPLC.

TABLE 6

| | Conversion | Yield, % | | | |
| --- | --- | --- | --- | --- | --- |
| | | p-NDPA | 4-NDPA | An Recr | Other |
| No KOH, TMACl Only | 0.0% | 0.0 | 0.0 | 0.0 | 0.0 |
| 1.30 grams KOH, 20 mmoles (0.5:1 vs NB) | 54.9% | 18.8 | 19.6 | 15.7 | 0.7 |
| 2.61 grams KOH, 40 mmoles (1:1 vs NB) | 69.2% | 21.3 | 26.8 | 20.8 | 0.3 |
| 5.22 grams KOH, 80 mmoles (2:1 vs NB) | 91.8% | 26.0 | 33.5 | 29.1 | 3.2 |
| 7.83 grams KOH, 120 mmoles (3:1 vs NB) | 97.1% | 25.2 | 35.5 | 30.6 | 5.8 |
| 10.44 grams KOH, 160 mmoles (4:1 vs NB) | 99.1% | 23.6 | 36.0 | 32.0 | 7.5 |
| 13.05 grams KOH, 200 mmoles (5:1 vs NB) | 100.5% | 21.5 | 36.0 | 32.0 | 11.1 |
| 15.66 grams KOH, 240 mmoles (6:1 vs NB) | 101.7% | 18.4 | 33.6 | 32.7 | 17.0 |

Higher excesses of base result in poorer reaction selectivity and more by-product formation. The same trend is observed when running the reaction under comparatively milder reaction conditions as described in Table 7 below. Similarly, conversion is a function of the amount of base used.

Aniline (99%, 32.60 grams, 346.5 mmoles), nitrobenzene (99%, 6.16 grams, 49.5 mmoles), potassium hydroxide in the amount given in Table 7 below (86% ground powder, 16.31 grams, 250 mmoles) and tetramethylammonium chloride (97%, 5.48 grams, 48.5 mmoles) were charge to a 100-mL round bottomed flask equipped with a Teflon paddle stirrer. The reaction was allowed to proceed for 1 hour with no application of external heat (some exotherm generated by dissolution of KOH in reaction water) in a stoppered flask. Contents were then sampled and analyzed by HPLC.

TABLE 7

| | Conversion | Yield, % | | | |
| --- | --- | --- | --- | --- | --- |
| | | p-NDPA | 4-NDPA | An Recr | Other |
| 9.77 grams KOH, 150 mmoles (3:1 vs NB) | 10.5% | 1.3 | 8.6 | 0.0 | 0.6 |
| 13.05 grams KOH, 200 mmoles (4:1 vs NB) | 64.6% | 14.9 | 26.2 | 15.4 | 8.1 |
| 16.31 grams KOH, 250 mmoles (5:1 vs NB) | 92.2% | 21.8 | 33.0 | 27.0 | 10.4 |
| 19.57 grams KOH, 300 mmoles (6:1 vs NB) | 100.5% | 21.7 | 33.6 | 31.8 | 13.5 |
| 22.84 grams KOH, 350 mmoles (7:1 vs NB) | 104.4% | 21.3 | 33.6 | 33.5 | 16.0 |

EXAMPLE 6

Example 6 indicates the effect that the introduction of an oxidant has on the conversion of aniline and nitrobenzene to p-NDPA, 4-NDPA and by-products when utilizing a potassium hydroxide/tetramethylammonium chloride base-PTC system.

Aniline (99%, 2.33 grams, 24.8 mmoles), nitrobenzene (99%, 3.08 grams, 20 24.8 mmoles), potassium hydroxide (86% ground powder, 9.77 grams, 150 mmoles), tetramethylammonium chloride (97%, 0.69 grams, 6.1 mmoles) and water (2.32 grams) was charged to a 50-mL round bottomed flask equipped with a magnetic stirrer. The reaction was allowed to proceed for 2 hours at 80° C. under atmospheric conditions described below. Contents were then sampled and analyzed by HPLC.

The definition of a closed system is a stoppered flask. An open system is left unstoppered and open to the atmosphere. For gas sweep experiments, a three-necked flask is substituted for a single-necked flask, the system equipped with both a gas inlet and outlet line, and the appropriate gas swept across the reaction mass at a low flow rate.

TABLE 8

| | Conversion | Selectivity | Yield, % | | | |
| --- | --- | --- | --- | --- | --- | --- |
| | | | p-NDPA | 4-NDPA | An Recr | Other |
| Closed System | 45.1% | 61.3% | 1.4 | 26.3 | 15.9 | 1.5 |
| Open System | 34.4% | 85.6% | 1.7 | 27.7 | 2.9 | 2.1 |
| Gas Sweep, Nitrogen | 94.8% | 58.2% | 2.4 | 52.8 | 38.3 | 1.3 |
| Gas Sweep, Air | 60.6% | 86.8% | 2.8 | 49.8 | 3.3 | 4.7 |

In cases where the reaction is left open to excess air, selectivity is markedly improved, as opposed to experiments where the amount of oxidant is limited. Formation of azobenzene is greatly increased in the latter instance.

Improvement in reaction selectivity is reinforced by experiments in Table 9, which demonstrate the effect of hydrogen peroxide addition in the reaction mixture.

Aniline (99%, 22.58 grams, 240 mmoles), nitrobenzene (99%, 4.97 grams, 40 mmoles), hydrogen peroxide (50% aqueous, amount indicated in Table 9 below), water (sum total from additional water and peroxide kept constant at 2.16 grams), potassium hydroxide (86% ground powder, 7.83 grams, 120 mmoles) and tetramethylammonium chloride (97%, 4.52 grams, 40 mmoles) was charged to a 50-mL round bottomed flask equipped with a magnetic stirrer:. Peroxide was charged to the reaction mixture before adding KOH & TMACI with the flask quickly stoppered and then the reaction was allowed to proceed for 1 hour at 60° C. Contents were then sampled and analyzed by HPLC.

TABLE 9

| | Yield, % | | | | | |
|---|---|---|---|---|---|---|
| | Conv | Selec | p-NDPA | 4-NDPA | An Recr | Other |
| No $H_2O_2$ & 2.16 g water | 96.6% | 67.9% | 27.9 | 37.7 | 30.6 | 0.5 |
| 0.27 g $H_2O_2$, 4 mmol, (0.1 vs NB) & 2.02 g water | 90.3% | 73.8% | 27.3 | 39.4 | 23.0 | 0.7 |
| 0.54 g $H_2O_2$, 8 mmol, (0.2 vs NB) & 1.89 g water | 86.6% | 77.7% | 27.3 | 40.0 | 18.3 | 1.0 |
| 1.09 g $H_2O_2$, 16 mmol, (0.4 vs NB) & 1.62 g water | 86.4% | 77.3% | 25.5 | 41.3 | 18.3 | 1.3 |
| 1.63 g $H_2O_2$, 24 mmol, (0.6 vs NB) & 1.34 g water | 86.4% | 78.4% | 26.9 | 40.9 | 17.6 | 1.1 |
| 2.18 g $H_2O_2$, 32 mmol, (0.8 vs NB) & 1.07 g water | 79.8% | 80.3% | 25.6 | 38.4 | 14.3 | 1.4 |
| 2.72 g $H_2O_2$, 40 mmol, (1.0 vs NB) & 0.80 g water | 80.8% | 82.0% | 25.9 | 40.4 | 13.0 | 1.6 |

The same trend noted for opening the reaction contents to air is also seen for peroxide, namely exposure to an oxidant improves selectivity. This observation is reinforced by experimental trials where excess nitrobenzene is used to act as an oxidant. (see Example 7).

EXAMPLE 7

Example 7 shows how the ratio of 4-ADPA intermediates can be controlled by adjusting the amount of aniline charged into the reaction.

Aniline (99%, amount given in Table 10), nitrobenzene (99%, 4.97 grams, 40 mmoles), potassium hydroxide (86% ground powder, 7.83 grams, 120 mmoles) and tetramethylammonium chloride (97%, 4.52 grams, 40 mmoles) was charged to 50- mL round bottomed flask equipped with magnetic stirrer. The reaction was allowed to proceed for 1 hour at 6020 C. in a stoppered flask. Contents were then sampled and analyzed by HPLC.

TABLE 10

| | Yield, % | | | | | |
|---|---|---|---|---|---|---|
| | Conv | Ratio | p-NDPA | 4-NDPA | An Recr | Other |
| 35.28 grams Aniline, 375 mmoles, 15:1 vs NB* | 87.2% | 1.34 | 36.7 | 27.3 | 22.2 | 1.1 |
| 36.69 grams Aniline, 390 mmoles, 13:1 vs NB^ | 93.2% | 1.31 | 37.1 | 28.4 | 26.3 | 1.4 |
| 36.22 grams Aniline, 385 mmoles, 11:1 vs NB# | 94.7% | 1.14 | 35.2 | 30.9 | 26.5 | 2.2 |
| 33.87 grams Aniline, 360 mmoles, 9:1 vs NB | 95.4% | 0.96 | 32.0 | 33.2 | 27.5 | 2.6 |
| 26.34 grams Aniline, 280 mmoles, 7:1 vs NB | 96.8% | 0.75 | 27.1 | 36.0 | 30.3 | 3.5 |
| 18.81 grams Aniline, 200 mmoles, 5:1 vs NB | 95.9% | 0.60 | 23.1 | 38.8 | 31.1 | 2.8 |
| 11.29 grams Aniline, 120 mmoles, 3:1 vs NB | 92.3% | 0.37 | 15.7 | 42.4 | 30.9 | 3.4 |
| 3.76 grams Aniline, 40 mmoles, 1:1 vs NB | 80.1% | 0.14 | 6.1 | 43.8 | 24.7 | 5.5 |

*25 mmole scale (35.28 gms aniline, 3.11 gms nitrobenzene, 4.89 gms KOH & 2.82 gms TMACl)
^30 mmole scale (36.69 gms aniline, 3.73 gms nitrobenzene, 5.87 gms KOH & 3.39 gms TMACl)
35 mmole scale (36.22 gms aniline, 4.35 gms nitrobenzene, 6.85 gms KOH & 3.95 gms TMACl)

As more aniline is charged to the reaction, more p-NDPA is formed relative to 4-NDPA. The same trend is noted under differing reaction conditions as outlined in Table 11 below.

Aniline (99%, amount given in Table 11), nitrobenzene (99%, 3.08 grams, 24.8 mmoles), potassium hydroxide (86% ground powder, 9.77 grams, 150 mmoles), tetramethylammonium chloride (97%, 0.69 grams, 6.1 mmoles) and water (Table 11, 20% w/w) was charged to a 50-mL round bottomed flask equipped with a magnetic stirrer. The reaction was allowed to proceed for 2 hours at 80° C. in an open flask. Contents were then sampled and analyzed by HPLC.

TABLE 11

| | Conv | Ratio | Yield, % | | | |
| | | | p-NDPA | 4-NDPA | An Recr | Other |
|---|---|---|---|---|---|---|
| 12.48 g An, 133 mmol, (5.4 vs NB) & 4.89 g H₂O | 18.6% | 0.52 | 5.6 | 10.9 | 1.0 | 1.1 |
| 8.57 g An, 91.1 mmol, (3.7 vs NB) & 3.90 g H₂O | 26.5% | 0.37 | 6.5 | 17.7 | 1.4 | 0.8 |
| 4.66 g An, 49.6 mmol, (2 vs NB) & 2.91 g H₂O | 28.9% | 0.12 | 2.6 | 20.9 | 3.2 | 2.1 |
| 2.33 g An, 24.8 mmol, (1 vs NB) & 2.32 g H₂O | 34.4% | 0.06 | 1.7 | 27.7 | 2.9 | 2.1 |
| 1.75 g An, 18.6 mmol, (.75 vs NB) & 2.17 g H₂O | 42.6% | 0.05 | 1.8 | 34.6 | 4.2 | 2.1 |
| 1.16 g An, 12.3 mmol, (.50 vs NB) & 2.02 g H₂O | 56.1% | 0.02 | 0.8 | 51.7 | 1.1 | 2.5 |
| 0.58 g An, 6.2 mmol, (.25 vs NB) & 1.88 g H₂O | 76.7% | 0.01 | 0.9 | 72.9 | 1.1 | 1.8 |

Yields of 4-ADPA intermediates (p-NDPA +4-NDPA) remain relatively flat when aniline is used in excess (approx. 20%) but improve significantly (73.8% at 0.25 to 1 An/NB) when aniline becomes the limiting reagent as noted in Table 11. Also, selectivity is improved (96.1% at 0.25 to 1 An/NB) when nitrobenzene is used in excess despite less overall water. As shown in Example 9, less water typically decreases selectivity in an inorganic base system. Excess nitrobenzene here acts as an oxidant, improving selectivity as shown in Example 6 with air and peroxide.

EXAMPLE 8

Example 8 illustrates that the reaction between aniline and nitrobenzene using potassium hydroxide as a base in conjunction with tetramethylammonium chloride can be conducted over a wide range of temperatures.

Aniline (99%, 2.33 grams, 24.8 mmoles), nitrobenzene (99%, 3.08 grams, 24.8 mmoles), potassium hydroxide (86% ground powder, 9.77 grams, 150 mmoles), tetramethylammonium chloride (97%, 0.69 grams, 6.1 mmoles) and water (2.32 grams, 20% w/w) was charged to a 50-mL round bottomed flask equipped with magnetic stirrer. The reaction was allowed to proceed for 2 hours at the given temperature in an open flask. Contents were then sampled and analyzed by HPLC.

TABLE 12

| | | Yield, % | | | |
| | Conversion | p-NDPA | 4-NDPA | An Recr | Other |
|---|---|---|---|---|---|
| Reaction Temperature, 20° C. | 9.3% | 0.1 | 8.3 | 0.0 | 1.0 |
| Reaction Temperature, 35° C. | 21.6% | 0.5 | 19.5 | 0.2 | 1.4 |
| Reaction Temperature, 50° C. | 25.2% | 0.8 | 22.3 | 0.1 | 1.9 |
| Reaction Temperature, 65° C. | 26.0% | 0.6 | 22.8 | 0.4 | 2.2 |
| Reaction Temperature, 80° C. | 34.4% | 1.7 | 27.7 | 2.9 | 2.1 |
| Reaction Temperature, 95° C. | 39.3% | 2.3 | 27.8 | 7.5 | 1.7 |

TABLE 12-continued

| | | Yield, % | | | |
| | Conversion | p-NDPA | 4-NDPA | An Recr | Other |
|---|---|---|---|---|---|
| Reaction Temperature, 110° C. | 53.8% | 3.5 | 33.4 | 12.8 | 4.0 |
| Reaction Temperature, 125° C. | 72.7% | 9.1 | 34.0 | 17.3 | 12.4 |

Increasing reaction temperature results in improved yields and conversion but reaction selectivity is lost. The amount of p-NDPA relative to 4-NDPA increases with increasing temperature.

TABLE 13

| | Yield, % | Selectivity, % | p-NDPA/4-NDPA |
|---|---|---|---|
| Reaction Temperature, 20° C. | 8.3 | 89.0 | 0.01 |
| Reaction Temperature, 35° C. | 20.0 | 92.3 | 0.03 |
| Reaction Temperature, 50° C. | 23.1 | 91.8 | 0.04 |
| Reaction Temperature, 65° C. | 23.4 | 90.0 | 0.03 |
| Reaction Temperature, 80° C. | 29.4 | 85.6 | 0.06 |
| Reaction Temperature, 95° C. | 30.1 | 76.7 | 0.08 |
| Reaction Temperature, 110° C. | 37.0 | 68.7 | 0.11 |
| Reaction Temperature, 125° C. | 43.1 | 59.2 | 0.27 |

EXAMPLE 9

Example 9 emphasizes the effect of water in the reaction of aniline and nitrobenzene with a KOH-TMACl base/phase transfer system to form 4-ADPA intermediates.

Aniline (99%, 22.58 grams, 240 mmoles), nitrobenzene (99%, 4.97 grams, 40 mmoles), potassium hydroxide (86% ground powder, 7.83 grams, 120 mmoles), tetramethylammonium chloride (97%, 4.52 grams, 40 mmoles), and water as listed in Tables 14 and 15 was charged to a 50-mL round bottomed flask equipped with a magnetic stirrer. The reaction was allowed to proceed for 1 hour at 60° C. in a stoppered flask. Contents were then sampled and analyzed by HPLC.

TABLE 14

|  | Conversion | Yield, % | | | |
|---|---|---|---|---|---|
|  |  | p-NDPA | 4-NDPA | An Recr | Other |
| No Water added | 98.6% | 26.4 | 38.5 | 30.4 | 3.3 |
| 2.16 grams H₂O, 120 mmoles (3:1 vs NB) | 94.7% | 28.5 | 37.3 | 28.6 | 0.4 |
| 4.32 grams H₂O, 240 mmoles (6:1 vs NB) | 67.0% | 27.2 | 21.1 | 18.4 | 0.3 |
| 6.48 grams H₂O, 320 mmoles (9:1 vs NB) | 28.3% | 16.3 | 6.7 | 5.1 | 0.2 |
| 8.64 grams H₂O, 480 mmoles (12:1 vs NB) | 5.5% | 4.1 | 1.3 | 0.0 | 0.0 |

TABLE 15

|  | Selectivity, % | p-NDPA/4-NDPA |
|---|---|---|
| No Water added | 65.8 | 0.69 |
| 3:1 H₂O/NB (1 mole Water vs. KOH) | 69.4 | 0.77 |
| 6:1 H₂O/NB (2 moles Water vs. KOH) | 72.1 | 1.28 |
| 9:1 H₂O/NB (3 moles Water vs. KOH) | 81.3 | 2.44 |
| 12:1 H₂O/NB (4 moles Water vs. KOH) | 100.0 | 3.08 |

A general improvement in selectivity and higher levels of p-NDPA relative to 4-NDPA becomes evident as the amount of water is increased.

The effect of too much water may also be noted from Example 2 and Table 3 where the effectiveness of a 60% aqueous solution of tetramethylammonium carbonate as a phase transfer catalyst is shown. Previous data obtained from a dilute 25% solution indicated practically no conversion.

EXAMPLE 10

Example 10 shows that the reaction may be carried out in any of several solvents.

Aniline (99%, 11.29 grams, 120 mmoles), nitrobenzene (99%, 2.49 grams, 20 mmoles), potassium hydroxide (86% ground powder, 3.91 grams, 60 mmoles), tetramethylammonium chloride (97%, 2.26 grams, 20 mmoles) and 20-mL of the appropriate solvent as represented in Table 16 was charged to a 50-mL round bottomed flask equipped with a magnetic stirrer. The reaction was allowed to proceed for 1 hour at 60° C. in a stoppered flask. Contents were then sampled and analyzed by HPLC.

TABLE 16

|  | Conversion | Yield, % | | | |
|---|---|---|---|---|---|
|  |  | p-NDPA | 4-NDPA | An Recr | Other |
| No solvent added | 97.1% | 25.2 | 35.5 | 30.6 | 5.8 |
| Dimethyl sulfoxide | 99.5% | 34.2 | 37.6 | 26.1 | 1.6 |
| Dimethyl sulfoxide, No phase transfer catalyst added | 36.5% | 10.9 | 15.8 | 6.4 | 3.4 |
| Benzyl ether | 93.7% | 30.6 | 32.1 | 28.1 | 3.0 |
| 1-Methyl-2-pyrrolidinone | 80.1% | 29.3 | 27.3 | 17.9 | 5.6 |
| N,N-Dimethylformamide | 74.0% | 27.2 | 27.2 | 19.1 | 0.6 |

TABLE 16-continued

|  | Conversion | Yield, % | | | |
|---|---|---|---|---|---|
|  |  | p-NDPA | 4-NDPA | An Recr | Other |
| p-Xylene | 65.9% | 8.8 | 10.1 | 44.6 | 2.4 |
| Toluene | 63.3% | 3.0 | 3.7 | 51.1 | 5.5 |

Notable is a roughly two-thirds reduction in yield when the phase transfer catalyst is omitted (26.7% in DMSO without TMACI increasing to 71.8% with TMACI).

Selectivity remains relatively unchanged in polar solvents (~70%) but plunges significantly when non-polar hydrocarbons such as p-xylene or toluene are selected as azobenzene yields in each of these two solvents exceed 40%.

EXAMPLE 11

Example 11 demonstrates the reaction of aniline and nitrobenzene in combination with an aqueous solution of potassium hydroxide and tetramethyalammonium chloride by continuous distillation of the aniline-water azeotrope.

111.8 grams aniline (99%, 1.19 moles), 31.2 grams aqueous potassium hydroxide solution (45%, 0.275 moles) and 50.0 grams aqueous tetramethylammonium chloride solution (55%, 0.25 moles) were charged to a 500-mL flask equipped with a Teflon paddle stirrer, thermocouple, nitrobenzene feed tube and needle valve. A vacuum was pulled on the mixture to 120 mm Hg, regulating pressure by bleeding air across the reactor. Heating was begun and nitrobenzene flow was started (24.6 grams, 99%, 0.20 moles) when the desired reaction temperature of 80° C. was reached. The temperature was controlled by increasing the vacuum so as to complete the NB feed in approximately one hour at a final pressure of 60 mm Hg. The pressure was held for 45 minutes at 60 mm Hg to insure completeness of reaction. The mixture was quenched with 40 mL of water. HPLC analysis: 32.1% aniline, 0% NB, 20.3% p-NDPA, 7.6% 4-NDPA, 0.50% t-azobenzene and 0.05% pheanzine. Yields based on 100% conversion of NB: 72.6% p-NDPA, 25.3%, 4-NDPA, 1.9% t-azobenzene, 0.2%, phenazine.

As shown in Table 17 below, running the identical reaction in the absence of air resulted in a 12% lower yield (97.9% vs. 85.5%) and a seven fold increase in the azobenzene level. A summary of other reactions in this series is also given in Table 17 below:

TABLE 17

| | Conversion | Selectivity | Yield, % | | | |
| --- | --- | --- | --- | --- | --- | --- |
| | | | p-NDPA | 4-NDPA | t-Azo | Phenazine |
| BASELINE: | | | | | | |
| See conditions below* | 100.0% | 97.9% | 72.6 | 25.3 | 1.9 | 0.2 |
| ATMOSPHERE: | | | | | | |
| Baseline conditions (Vacuum, No Air) | 100.0% | 85.5% | 66.5 | 19.0 | 14.2 | 0.3 |
| ANILINE CHARGE: | | | | | | |
| 74.5 gms Aniline, 0.79 moles, 4:1 vs NB | 99.5% | 96.2% | 56.4 | 39.8 | 2.7 | 0.5 |
| 149.0 gms Aniline, 1.58 moles, 8:1 vs NB | 100.0% | 97.9% | 73.8 | 24.1 | 1.8 | 0.3 |
| TEMPERATURE | | | | | | |
| 70° C. | 100.0% | 98.1% | 65.1 | 33.0 | 1.4 | 0.5 |
| 90° C. | 100.0% | 97.1% | 71.9 | 25.1 | 2.7 | 0.2 |
| NITROBENZENE FEED RATE: | | | | | | |
| 29 minutes | 100.0% | 85.2% | 62.7 | 22.5 | 14.4 | 0.4 |
| 86 minutes | 99.9% | 96.1% | 76.8 | 19.2 | 3.5 | 0.4 |
| BASE CHARGE: | | | | | | |
| 18.7 g 45% KOH, 0.15 mol, 0.75:1 vs NB | 83.0% | 97.6% | 63.1 | 17.9 | 1.8 | 0.2 |
| 37.4 g 45% KOH, 0.30 mol, 1.5:1 vs NB | 100.0% | 96.9% | 72.7 | 24.2 | 2.7 | 0.4 |
| ATMOSPHERE: | | | | | | |
| Vacuum, No Air | 100.0% | 85.5% | 66.5 | 19.0 | 14.2 | 0.3 |

*6:1 Aniline/NB, 80° C., 49 min. NB feed time, 1.25 moles KOH vs NB, air atmosphere

We claim:
1. A method of producing one or more 4-aminodiphenylamine intermediates comprising the steps of:
   (a) bringing an aniline or aniline derivative and nitrobenzene into reactive contact; and
   (b) reacting the aniline and nitrobenzene in a confined zone at a suitable time and temperature, in the presence of a mixture comprising a strong base, an oxidant and a phase transfer catalyst selected from the group of compounds defined by (b) reacting the aniline and nitrobenzene in a confined zone at a suitable time and temperature, in the presence of a mixture comprising a strong base, an oxidant, and a phase transfer catalyst selected from the group of compounds defined by:

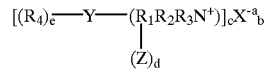

$$[(R_4)_e\!\!-\!\!Y\!\!-\!\!(R_1R_2R_3N^+)]_c X^{-a}{}_b$$
$$\phantom{[(R_4)_e\!\!-\!\!Y\!\!-}(Z)_d$$

where $R_1$, $R_2$, $R_3$ are the same or different and selected from any straight chain or branched alkyl group containing from $C_1$ to $C_{20}$, $(R_4)_e$ is hydrogen for e=0, $R_4$ is $R_1R_2R_3N^+$ for e=1 or 2, Y is alkyl, aryl, alkyl aryl or benzyl and substituted derivatives thereof, Z is a substituent selected from the group consisting of hydroxyl, halo, and other hetero atoms, X is an anionic moiety of the form fluoride, chloride, hydroxide, sulfate, hydrogensulfate, acetate, formate, nitrate, phosphate, hydrogen phosphate, dihydrogenphosphate, oxalate, carbonate, borate, tartrate, citrate, malonate and mixtures of said compounds, where a=the valence of the anionic moiety (1, 2 or 3), b and c are whole number integers of value 1, 2 or 3 and d is a whole number integer of value 0 to 4.

2. The method of claim 1 wherein said phase transfer catalyst is selected from the group consisting of tetramethylammonium chloride, tetramethylammonium fluoride, tetramethylammonium hydroxide, bis-tetramethylammonium carbonate,
   tetramethylammonium formate and tetramethylammonium acetate;
   tetrabutylammonium hydrogensulfate and tetrabutylammonium sulfate;
   methyltributylammonium chloride; and benzyltrimethylammonium hydroxide, tricaprylylmethylammonium chloride, tetrabutylammonium chloride, tetramethylammonium nitrate, cetyltrimethylammonium chloride and choline hydroxide.

3. The method of claim 1 wherein the molar ratio of phase transfer catalyst to nitrobenzene is from about 0.05:1 to about 1.2:1.

4. The method of claim 1 wherein said aniline derivative is selected from the group consisting of formanilide, phenylurea, carbanilide and thiocarbanilide.

5. The method of claim 1 wherein said aniline is a substituted aniline selected from the group consisting of 2-methoxyaniline, 4-methoxyaniline, 4-chloroaniline, p-toluidine, 4-nitroaniline, 3-bromoaniline, 3-bromo-4-aminotoluene, p-aminobenzoic acid, 2,4-diaminotoluene, 2,5-dichloroaniline, 1,4-phenylene diamine, 4,4'-methylene dianiline, 1,3,5-triaminobenzene, and mixtures thereof.

6. The method of claim 1 wherein substituted nitrobenzenes that may be used in accordance with the process of the present invention include o- and m-methylnitrobenzene, o- and m-ethylnitrobenzene, o - and m-methoxynitrobenzene, and mixtures thereof.

7. The method of claim 1 wherein said strong base is selected from the group consisting of potassium hydroxide, sodium hydroxide, cesium hydroxide, rubidium hydroxide and potassium-t-butoxide.

8. The method of claim 1 wherein the mole ratio of strong base to nitrobenzene is greater than about 1:1.

9. The method of claim 1 wherein the mole ratio of strong base to nitrobenzene is about 2:1 to about 6:1.

10. The method of claim 1 wherein said oxidant is free oxygen.

11. The method of claim 1 wherein said oxidant is an oxidizing agent.

12. The method of claim 11 wherein said oxidizing agent is a peroxide.

13. The method of claim 11 wherein said oxidizing agent is hydrogen peroxide.

14. The method of claim 11 wherein said oxidizing agent is nitrobenzene.

15. The method of claim 1 wherein said reactive contact is carried out at a temperature of from about 20° C. to about 125° C. a pressure in the range of from about 20 mbar to about atmospheric and a reaction time less than about 3.5 hours.

16. The method of claim 1 wherein the reaction of step (b) is carried out in the presence of not greater than about 10:1 moles water to moles nitrobenzene excluding water of hydration.

17. The method of claim 1 wherein said mixture comprising a strong base and a phase transfer catalyst is in aqueous solution and the reaction is carried out with a continuous distillation of aniline-water azeotrope.

18. The method of claim 1 wherein said reactive contact occurs in a suitable solvent system.

19. The method of claim 18 wherein said suitable solvent system comprises a polar aprotic solvent.

20. The method of claim 19 wherein said polar aprotic solvent is selected form the group consisting of dimethyl sulfoxide, benzyl ether, 1-Methyl-2-pyrrolidinone and N,N-dimethylformamide.

21. The method of claim 1 wherein said intermediates are hydrogenated to produce 4-aminodiphenylamine.

22. A method of producing one or more 4-aminodiphenylamine intermediates comprising the steps of:
a. bringing an aniline or aniline derivative and nitrobenzene into reactive contact; and
b. reacting the aniline and nitrobenzene in a confined zone at a suitable time and temperature in the presence of a mixture comprising an oxidant and a strong base that also functions as a phase transfer catalyst selected from the group of compounds defined by:

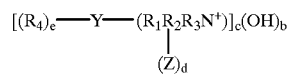

I where $R_1$, $R_2$, $R_3$ are the same or different and selected from any straight chain or branched alkyl group containing from $C_1$ to $C_{20}$, $(R_4)_e$ is hydrogen for e=0, $R_4$ is $R_1R_2R_3N^+$ for e=1 or 2, Y is alkyl, aryl, alkyl aryl or benzyl and substituted derivatives thereof, Z is a substituent selected from the group consisting of hydroxyl, halo, and other hetero atoms, b and c are whole number integers of value 1, 2 or 3 and d is a whole number integer of value 0 to 4.

23. The method of claim 22 wherein said strong base that also functions as a phase transfer catalyst comprises tetramethylammonium hydroxide and/or benzyltrimethylammonium hydroxide.

24. The method of claim 22 wherein said oxidant comprises hydrogen peroxide.

25. The method of claim 22 wherein the reaction in the confined zone is carried out in the absence of an alkali metal hydroxide.

26. The method of claim 22 wherein said intermediates are hydrogenated to produce 4-aminodiphenylamine.

* * * * *

UNITED STATES PATENT AND TRADEMARK OFFICE
CERTIFICATE OF CORRECTION

PATENT NO. : 6,395,933 B1
DATED : May 28, 2002
INVENTOR(S) : Triplett, II et al.

It is certified that error appears in the above-identified patent and that said Letters Patent is hereby corrected as shown below:

Column 1,
Line 51, "processes processes for preparing" should read -- processes for preparing --

Column 2,
Lines 3-7, the recitation "compounds defined by (b) reacting the aniline and nitrobenzene in a confined zone at a suitable time and temperature, in the presence of a mixture comprising a strong base, an oxidant and a phase transfer catalyst selected from the group of compounds defined by:" should read -- compounds defined by: --

The formula    I

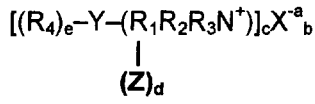

should read -- 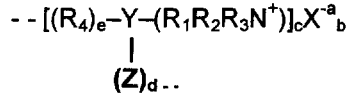 --    I

Column 4,
The formula    I

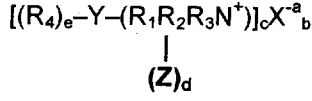

should read -- 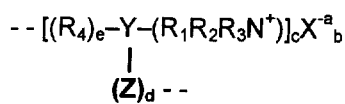 --    II

Line 44, "$(R_4)[<i]$nfe is hydrogen" should read -- $(R_4)_e$ is hydrogen --

UNITED STATES PATENT AND TRADEMARK OFFICE
CERTIFICATE OF CORRECTION

PATENT NO. : 6,395,933 B1
DATED : May 28, 2002
INVENTOR(S) : Triplett, II et al.

It is certified that error appears in the above-identified patent and that said Letters Patent is hereby corrected as shown below:

Column 4, cont'd.
Line 58, "reaction mixtures." should read -- reaction mixtures, except where indicated. --
Line 61, "0.6 grams" should read -- 0.06 grams --
Table 3, 15$^{th}$ line down, "Tricaprylylmethylammonium chloride, 99+%, should read -- Tricaprylmethylammonium chloride, 99+%, --

Column 19,
Claim 1, the formula

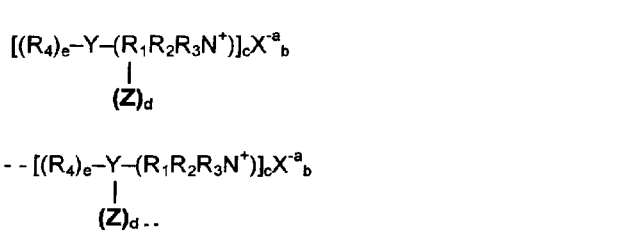

should read

Lines 44-48, "compounds defined by (b) reacting the aniline and nitrobenzene in a confined zone at a suitable time and temperature, in the presence of a mixture comprising a strong base, an oxidant and a phase transfer catalyst selected from the group of compounds defined by:" should read -- compounds defined by: --

Column 20,
Line 48, Claim 2, "tricaprylylmethylammonium" should read -- tricaprylmethylammonium --

UNITED STATES PATENT AND TRADEMARK OFFICE
CERTIFICATE OF CORRECTION

PATENT NO. : 6,395,933 B1
DATED : May 28, 2002
INVENTOR(S) : Triplett, II et al.

It is certified that error appears in the above-identified patent and that said Letters Patent is hereby corrected as shown below:

Column 22,
Claim 22, the formula $$[(R_4)_e-Y-(R_1R_2R_3N^+)]_c X^{-a}_b \quad \text{I}$$
$$\;|\;$$
$$(Z)_d$$

should read --

$$[(R_4)_e-Y-(R_1R_2R_3N^+)]_c X^{-a}_b \quad \text{--II}$$
$$\;|\;$$
$$(Z)_d \text{ --}$$

Signed and Sealed this

Third Day of December, 2002

JAMES E. ROGAN
*Director of the United States Patent and Trademark Office*